United States Patent [19]

Kaplan

[11] Patent Number: 4,558,062

[45] Date of Patent: Dec. 10, 1985

[54] DIPHENYLAZOMETHINES BEARING AN IMIDAZOLYL GROUP AND PHARMACEUTICAL COMPOSITIONS CONTAINING THEM

[75] Inventor: Jean-Pierre Kaplan, Bourg la Reine, France

[73] Assignee: Synthelabo, Paris, France

[21] Appl. No.: 626,298

[22] Filed: Jun. 29, 1984

[30] Foreign Application Priority Data

Jul. 1, 1983 [FR] France ................................ 83 10974

[51] Int. Cl.⁴ .................... A61K 31/415; C07D 233/64
[52] U.S. Cl. ..................................... 514/400; 548/342; 548/343
[58] Field of Search ............................... 548/342, 324; 424/273 R; 514/400

[56] References Cited

PUBLICATIONS

Morrison and Boyd, "Organic Chemistry", 4 Ed. 1983, pp. 900–901.

*Primary Examiner*—Richard A. Schwartz
*Assistant Examiner*—Kurt G. Briscoe
*Attorney, Agent, or Firm*—Wegner & Bretschneider

[57] ABSTRACT

Diphenylazomethines of the formula

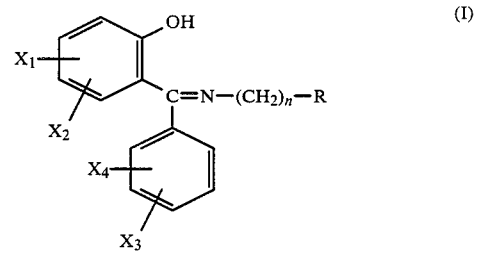

in which $X_1$, $X_2$, $X_3$ and $X_4$, which may be the same or different, each represent a hydrogen or halogen atom or a nitro, cyano, hydroxy, methoxy, $C_1$-$C_3$-alkyl, allyl or phenyl group, and either R represents a 2-(1H-imidazolyl) radical and n is 1 or R represents a 4-(1H-imidazolyl) radical and n is 1 or 2 have antidepressant, analgesic and antiulcerative properties.

6 Claims, No Drawings

DIPHENYLAZOMETHINES BEARING AN IMIDAZOLYL GROUP AND PHARMACEUTICAL COMPOSITIONS CONTAINING THEM

The present invention relates to diphenylazomethines bearing an imidazolyl radical, their preparation and their application in therapeutics.

The diphenylazomethines of the invention are of the formula

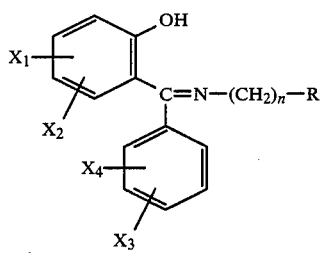

in which $X_1$, $X_2$, $X_3$ and $X_4$, which may be the same or different, each represent a hydrogen or halogen atom or a nitro, cyano, hydroxy, methoxy, $C_1$–$C_3$-alkyl, allyl or phenyl group, and either R represents a 2-(1$\underline{H}$-imidazolyl) radical and n is 1 or R represents a 4-(1$\underline{H}$-imidazolyl) radical and n is 1 or 2.

Preferred diphenylazomethines formula (I) are those in which $X_1$ and $X_3$ each represent a hydrogen, fluorine, chlorine or bromine atom, and $X_2$ represents a hydrogen atom or methyl or allyl group.

According to the invention, the diphenylazomethines of formula (I) can be prepared by reacting a benzophenone of the formula

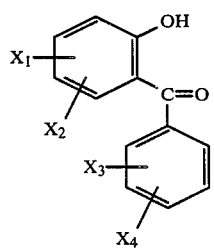

with a compound of formula $H_2N(CH_2)_nR$ (III) or a hydrochloride thereof, the various symbols in (II) and (III) being as defined above.

The reaction between the benzophenone (II) which has been described in French Patents Nos. 75/24,065, 76/21,922 or 81/21,559 (Synthelabo), and the compound (III) can be suitably performed in a solvent such as methanol, ethanol or toluene, if necessary in the presence of a base such as sodium bicarbonate, sodium carbonate, sodium methoxide or sodium ethoxide, at a temperature of 20° to 110° C.

The compounds (III) are prepared from compounds described in the literature according to methods described in the literature.

The Examples which follow illustrate the invention.

The structures of the compounds were conformed by microanalyses and IR and NMR spectra.

EXAMPLE 1

4-Chloro-2-[(2-chlorophenyl)-{[4-(1$\underline{H}$-imidazolyl)methyl]imino}methyl]phenol

[$X_1$=4-Cl, $X_2$=H, $X_3$=2-Cl, $X_4$=H, n=1, R=4-(1$\underline{H}$-imidazolyl)]

2.67 g (0.009 mole) of 5-chloro-2-hydroxyphenyl 2-chlorophenyl ketone, 2.21 g (0.013 mole) of 4-imidazolylmethylamine dihydrochloride,, 2.2 g (0.026 mole) of $NaHCO_3$ and 20 ml of absolute ethanol are introduced into an Erlenmeyer flask. This mixture is brought to refluxing temperature, and refluxed for 24 hours. The reaction mixture is evaporated to dryness, and the residue taken up with water and methylene chloride. The insoluble material is filtered off and washed several times with ether. A yellow solid is obtained. The organic phase is washed with water, dried over $MgSO_4$ and evaporated. A yellow solid is obtained which is identical to the above.

M.P.=228°–230° C.

EXAMPLE 2

4-Chloro-2-[(2-bromophenyl)- [2-(4-1$\underline{H}$-imidazolyl]) ethyl]imino methyl]phenol

[$X_1$=4-Cl, $X_2$=H, $X_3$=2-Br, $X_4$=H, n=2, R=4 (1$\underline{H}$-imidazolyl]

10.3 G of 5-chloro-2-hydroxyphenyl 2-bromophenyl ketone and 250 ml of methanol are introduced into a 500 ml round-bottomed flask, and then 6.15 g of histamine hydrochloride and 3.6 g of sodium methoxide are added. The mixture is evaporated to dryness, 250 ml of ethanol are added and the mixture is again evaporated to dryness. The residue is taken up in chloroform, the chloroform phase washed with water, the mixture left for decanting and the separated organic phase dried over $MgSO_4$. The solid is filtered off on a sinter. The filtrate is evaporated to dryness, and the product crystallised in petroleum ether. After recrystallisation, it is dried in a dessicator.

M.P.=178.4° C.

Details of compounds of the invention, prepared by way of example, are collated in the following Table.

TABLE

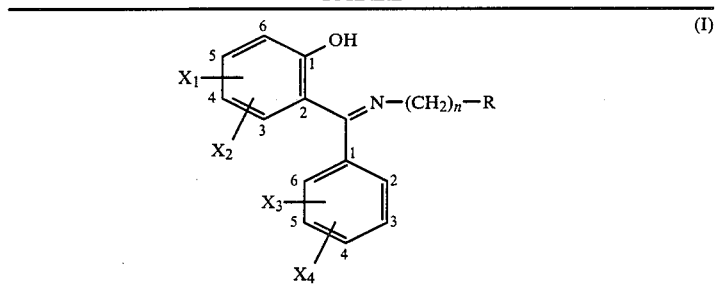

(I)

| Compound | $X_1$ | $X_2$ | $X_3$ | $X_4$ | n | R(*) | M.p. (°C.) |
|---|---|---|---|---|---|---|---|
| 1 | 4-Cl | H | 2-Br | H | 2 | (4) | 178.4 |
| 2 | 4-F | H | 4-Cl | H | 2 | (4) | 176.7 |
| 3 | 4-Cl | H | 2-Cl | H | 1 | (2) | 113–114 |
| 4 | 4-Cl | H | 2-Cl | H | 1 | (4) | 228–230 |
| 5 | 4-Cl | 6-$CH_3$ | 4-Cl | H | 1 | (4) | 179–180 |
| 6 | 4-Cl | H | 2-Cl | H | 2 | (4) | 168–168 |
| 7 | 4-Cl | H | H | H | 1 | (4) | 167–168 |
| 8 | 4-Cl | H | 2-Cl | 4-Cl | 1 | (4) | 212–213 |
| 9 | 4-Cl | H | 2-$CH_3$ | 5-$CH_3$ | 1 | (4) | 128 |
| 10 | 6-Cl | 4-Cl | 2-Cl | H | 1 | (4) | 224–225 |
| 11 | 4-$NO_2$ | H | H | H | 1 | (4) | 162–163 |
| 12 | 4-Cl | H | 2-Br | H | 1 | (4) | 230–231 |
| 13 | 4-Cl | H | 2-F | H | 1 | (4) | 202–203 |
| 14 | 4-$CH_3$ | H | 2-$CH_3$ | 5-$CH_3$ | 1 | (4) | 183–184 |
| 15 | 4-Br | H | 2-Cl | H | 1 | (4) | 240–241 |
| 16 | 6-$CH_3$ | 4-Cl | H | H | 1 | (4) | 179–180 |
| 17 | H | H | H | H | 1 | (4) | 154–155 |
| 18 | 4-Cl | H | 4-$CH_3$ | H | 1 | (4) | 202–203 |
| 19 | 4-Cl | H | 2-$CH_3$ | H | 1 | (4) | 166–167 |
| 20 | 4-F | H | 4-Cl | H | 1 | (4) | 147–148 |
| 21 | 4-Br | H | 2-Cl | 4-Cl | 1 | (4) | 212–213 |
| 22 | 4-$CH_3$ | H | H | H | 1 | (4) | 170–171 |
| 23 | 4-Cl | H | 4-Cl | H | 1 | (4) | 189–190 |
| 24 | 6-$CH_2CH_2CH_3$ | 4-Cl | 4-Cl | H | 1 | (4) | 178–180 |
| 25 | 4-$CH_3$ | H | 2-Cl | H | 1 | (4) | 194–195 |
| 26 | 5-$CH_3$ | 4-$CH_3$ | 2-Cl | H | 1 | (4) | 148–149 |
| 27 | 5-$CH_3$ | 4-Cl | 2-Cl | H | 1 | (4) | 190–191 |
| 28 | 5-$CH_3$ | 4-Cl | H | H | 1 | (4) | 163–164 |
| 29 | 6-Cl | 4-Cl | H | H | 1 | (4) | 228–229 |
| 30 | 6-$CH_2CH=CH_2$ | 4-Cl | H | H | 1 | (4) | 177–178 |
| 31 | H | H | 3-Cl | 4-Cl | 1 | (4) | 164–165 |
| 32 | 5-Cl | 4-Cl | H | H | 1 | (4) | 190–191 |
| 33 | 4-Cl | H | 3-Cl | H | 1 | (4) | 141–142 |
| 34 | 6-$CH_3$ | 4-Cl | 3-Cl | 4-Cl | 1 | (4) | 174–175 |
| 35 | 6-$C_2H_5$ | 4-Cl | 4-$C_2H_5$ | H | 1 | (4) | 140–142 |
| 36 | 6-$CH_2CH=CH_2$ | 4-Cl | 2-Cl | H | 1 | (4) | 93–95 |
| 37 | 4-$C_6H_5$ | H | H | H | 1 | (4) | 219–220 |
| 38 | 4-Cl | 3-Cl | H | H | 1 | (4) | 165–166 |
| 39 | 6-Cl | 5-Cl | H | H | 1 | (4) | 222–223 |
| 40 | 6-Cl | 5-Cl | 2-F | H | 1 | (4) | 217–218 |
| 41 | H | H | 2-Cl | H | 1 | (4) | 158–159 |
| 42 | 6-Cl | 3-Cl | 2-Cl | H | 1 | (4) | 133–134 |
| 43 | 5-Cl | 4-Cl | 2-Cl | H | 1 | (4) | 207–208 |
| 44 | 6-$C_6H_5$ | H | H | H | 1 | (4) | 238–240 |
| 45 | 5-Cl | 3-Cl | H | H | 1 | (4) | 183–184 |
| 46 | 4-$C_6H_5$ | H | 2-F | H | 1 | (4) | 206–207 |
| 47 | 6-CN | H | H | H | 1 | (4) | 194–195 |
| 48 | 6-$C_6H_5$ | H | 2-Cl | H | 1 | (4) | 181–182 |
| 49 | 4-$C_6H_5$ | H | 2-Cl | H | 1 | (4) | 244–245 |
| 50 | 6-Cl | 5-Cl | 2-Cl | H | 1 | (4) | 238–239 |
| 51 | H | H | 2-OH | H | 1 | (4) | 244–245 |
| 52 | 4-Cl | H | H | H | 2 | (4) | 148–149 |
| 53 | 4-Cl | H | 2-F | H | 2 | (4) | 133–134 |
| 54 | 6-$CH_3$ | 4-Cl | 4-Cl | H | 2 | (4) | 139–140 |
| 55 | 4-Cl | H | 4-$CH_3$ | H | 2 | (4) | 159–160 |
| 56 | 4-$CH_3$ | H | H | H | 2 | (4) | 200–201 |
| 57 | 5-$CH_3$ | 4-Cl | 2-Cl | H | 2 | (4) | 162–163 |
| 58 | 5-$CH_3$ | 4-Cl | H | H | 2 | (4) | 155–156 |
| 59 | 4-Cl | H | 3-$CH_3$ | H | 2 | (4) | 181–182 |
| 60 | 4-Cl | H | 2-$CH_3$ | H | 2 | (4) | 188–189 |
| 61 | 6-$CH_3$ | 4-Cl | H | H | 2 | (4) | 157–158 |
| 62 | 4-Cl | H | 4-Cl | H | 2 | (4) | 162–163 |
| 63 | 4-Cl | H | 3-Cl | H | 2 | (4) | 177–178 |
| 64 | 5-$CH_3$ | 4-Cl | H | H | 2 | (4) | 161–162 |
| 65 | H | H | H | H | 2 | (4) | 145–146 |
| 66 | 4-$CH_3$ | H | H | H | 1 | (2) | 194–196 |
| 67 | 4-Cl | H | 2-F | H | 1 | (2) | 180–182 |

TABLE-continued

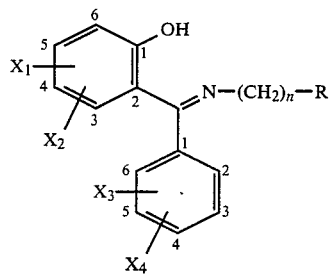

(I)

| Compound | X₁ | X₂ | X₃ | X₄ | n | R(*) | M.p. (°C.) |
|---|---|---|---|---|---|---|---|
| 68 | 4-Cl | H | 2-CH₃ | 5-CH₃ | 1 | (2) | 164–166 |
| 69 | H | H | H | H | 1 | (2) | 182–184 |
| 70 | 4-CH₃ | H | 2-Cl | H | 1 | (2) | 181–183 |
| 71 | 4-CL | H | H | H | 1 | (2) | 207–208 |
| 72 | 4-Cl | H | 2-Cl | H | 1 | (2) | 113–114 |
| 73 | 5-OCH₃ | H | H | H | 1 | (4) | 172–174 |
| 74 | 6-CH₃ | 4-CH₃ | H | H | 1 | (4) | 162–164 |

(*): (2) represents 2-(1H-imidazolyl)
(4) represents 4-(1H-imidazolyl)

The compounds of the invention were tested pharmacologically. Their analgesic activity was shown in the test of Koster et al. (acetic acid writhing test in mice), Fed. Proc., 18, 412, 1959.

The compound to be tested is administered orally to 30 fasted mice in 1% solution in Tween 80, in the proportion of 0.2 ml per 20 g of body weight; 30 minutes later, acetic acid (in 0.6% solution in a mixture of carboxymethylcellulose and Tween 80, in the proportion of 10 ml per kg of body weight) is administered intraperitoneally. The total number of contortions is noted during a 15-minute period.

The percentage of protection is determined relative to a control batch, and the $ED_{50}$ determined by graphic means (dose which protects 50% of animals).

The $ED_{50}$ of the compounds of the invention ranges from 20 to 200 mg/kg, administered orally.

The compounds also have antidepressant activity, antidyskinetic activity and antiulcerative activity, and they reduce the secretion of the gastric acid.

The antiulcerative activity of the compounds was shown in the tests on stress-induced ulcers and phenylbutazone-induced ulcers.

Stress-induced ulcer

The technique used is that of Senay and Levine, Proc. Soc. Exp. Biol. 1967, 124, 1221–1223 and Peptic Ulcers, edited by C. J. PFEIFER, pp. 92–97, on Wistar female rats weighing 180–210 g, fasted for 20 hours and distributed in random groups.

The animals are put under restraint in cylindrical boxes 20 cm×5 cm, and placed in a cold room in which the temperature is maintained at 2°–4° C.

The compounds to be studied are administered orally in the proportion 10, 30 and 100 mg/kg immediately before putting the animals under restraint, the control rats receiving only the placebo.

2 hours later, the animals are sacrificed by inhalation of chloroform.

The stomachs are removed and the degree of ulceration noted.

The compounds of the invention significantly reduce ($\leq$-92%) the stress-induced ulcers.

Phenylbutazone-induced ulcer

The test is carried out on Wistar female rats weighing 180–210 g, fasted for 20 hours and distributed in random groups.

The ulcers are provoked by the oral administration of phenylbutazone in solution mole-for-mole with NaOH, at the dose of 200 mg/kg.

The compounds to be studied are administered orally in the proportion of 100 mg/kg, 30 minutes before the ingestion of phenylbutazone, the control animals only receiving the placebo.

Two hours after the administration of the ulcerogenic agent, the animals are sacrificed by inhalation of chloroform.

The stomachs are removed and the degree of ulceration noted.

The compounds of the invention significantly reduce (almost 100%) the phenylbutazone-induced ulcers.

The acute toxicity of the compounds was determined. The $LD_{50}$ when administered orally varies from 70 to more than 1,000 mg/kg.

The compounds of the invention possess antidepressant, analgesic and antiulcerative properties, and can thus be used for the treatment of depression, pain of diverse origins (for example post-operative, dental or migraines) and gastric, duodenal or gastro-duodenal ulcers.

The compounds of the invention can be administered orally or parenterally, in the form of pharmaceutical compositions containing the active substance in association with any suitable excipient; for example, in the form of tablets, sugar-coated pills, gelatin capsules, capsules generally or solutions or suspensions to be taken orally or injected.

The daily dosage can range from 10 to 2,000 mg.

I claim:

1. A diphenylazomethine of the formula

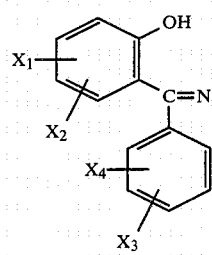 (I)

in which $X_1$, $X_2$, $X_3$ and $X_4$, are independently selected from hydrogen and halogen atoms and nitro, cyano, hydroxy, methoxy, $C_1$–$C_3$-alkyl, allyl and phenyl groups, and either R represents a 2-(1H-imidazolyl) radical and n is 1 or R represents a 4-(1H-imidazolyl) radical and n is 1 or 2.

2. A compound according to claim 1, in which $X_1$ and $X_3$ are independently selected from hydrogen, fluorine, chlorine and bromine atoms, and $X_2$ is selected from a hydrogen atom and methyl and allyl groups.

3. 4-Chloro-2-[(2-chlorophenyl)-{[4-(1H-imidazolylmethyl]imino}methyl]phenol.

4. A pharmaceutical composition for treating depression comprising an antidepressant effective amount of a diphenylazomethine of claim 1 and a pharmaceutically acceptable excipient.

5. A pharmaceutical composition providing an analgesic effect comprising an analgesically effective amount of a diphenylazomethine of claim 1 and a pharmaceutically acceptable excipient.

6. A pharmaceutical composition providing an antiulcerative effect comprising an antiulcerative effective amount of a diphenylazomethine of claim 1 and a pharmaceutically acceptable excipient.

* * * * *